United States Patent [19]

Wu et al.

[11] Patent Number: 5,306,851

[45] Date of Patent: Apr. 26, 1994

[54] HIGH VISCOSITY INDEX LUBRICANT FLUID

[75] Inventors: Margaret M. Wu, Skillman, N.J.; Dong-Ming Shen, Langhorne, Pa.; Catherine S. H. Chen, Berkeley Heights, N.J.

[73] Assignee: Mobil Oil Corporation, Fairfax, Va.

[21] Appl. No.: 979,962

[22] Filed: Nov. 23, 1992

[51] Int. Cl.$^5$ .................. C10M 127/00; C07C 13/615
[52] U.S. Cl. ..................................... 585/22; 585/352; 585/21; 252/9
[58] Field of Search ................. 252/9; 585/22, 21, 352

[56] References Cited

U.S. PATENT DOCUMENTS

| | | | |
|---|---|---|---|
| 3,648,531 | 3/1972 | Duling et al. | 74/200 |
| 3,671,598 | 6/1972 | Moore | 260/666 M |
| 3,671,600 | 6/1972 | Moore | 260/666 M |
| 3,793,203 | 2/1974 | Driscoll et al. | 252/56 R |
| 3,903,001 | 9/1975 | Gates et al. | 252/32.7 E |
| 3,966,624 | 6/1976 | Duling et al. | 252/52 R |
| 3,972,243 | 8/1976 | Driscoll et al. | 74/200 |
| 3,972,941 | 8/1976 | Driscoll et al. | 260/593 R |
| 3,994,816 | 11/1976 | Wygant | 252/73 |
| 4,008,251 | 2/1977 | Moore et al. | 260/333 |
| 4,043,927 | 8/1977 | Duling et al. | 252/52 R |
| 4,329,529 | 5/1982 | Nambu | 585/20 |
| 4,371,726 | 2/1983 | Horita et al. | 585/3 |
| 4,675,459 | 6/1987 | Yuasa et al. | 585/21 |
| 4,751,335 | 6/1988 | Kubo et al. | 585/7 |
| 4,761,510 | 8/1988 | Naruse et al. | 585/268 |
| 4,783,565 | 11/1988 | Naruse et al. | 585/268 |
| 4,786,427 | 11/1988 | Dare-Edwards | 252/56 |
| 4,889,649 | 12/1989 | Murai et al. | 252/73 |
| 4,913,794 | 4/1990 | Le et al. | 208/18 |
| 5,017,734 | 5/1991 | Baum et al. | 585/22 |
| 5,019,660 | 5/1991 | Chapman et al. | 585/22 |
| 5,043,503 | 8/1991 | DelRossi et al. | 585/360 |
| 5,053,568 | 10/1991 | Chen | 585/21 |
| 5,085,792 | 2/1992 | Narihiko et al. | 252/79 |
| 5,107,041 | 4/1992 | Abe et al. | 585/20 |

OTHER PUBLICATIONS

M. Muraki and Y. Kimura, Traction Characteristics of Synthetic Hydrocarbon Oils, 7 Journal of JSLE 119 (Int'l. Edition, 1986).

14 Kirk–Othmer Encyclopedia of Chemical Technology, 489 (Wiley, 1981).

*Primary Examiner*—Jacqueline V. Howard
*Attorney, Agent, or Firm*—Alexander J. McKillop; Dennis P. Santini; Robert B. Furr, Jr.

[57] ABSTRACT

The invention provides a composition comprising at least about 10 different diamondoid compounds selected from the group consisting of methyl-substituted and ethyl-substituted adamantane, diamantane, and triamantane, wherein each of said selected diamondoid compounds comprises no more than about 10 weight percent of said composition. The composition is useful as high quality lubricating fluid and exhibits the unusual combination of high Viscosity Index and very low pour point.

18 Claims, No Drawings

HIGH VISCOSITY INDEX LUBRICANT FLUID

FIELD OF THE INVENTION

This invention relates to the field of novel lubricant base fluids. More specifically, this invention provides a lubricant composition having a combination of usually high Viscosity Index and high traction coefficient.

BACKGROUND OF THE INVENTION

Efforts to improve upon the performance of natural mineral oil based lubricants by the synthesis of oligomeric hydrocarbon fluids have been the subject of important research and development in the petroleum industry for at least fifty years and have led to the relatively recent market introduction of a number of superior polyalpha-olefin synthetic lubricants, primarily based on the oligomerization of alpha-olefins or 1-alkenes. In terms of lubricant property improvement, the thrust of the industrial research effort on synthetic lubricants has been toward fluids exhibiting useful viscosities over a wide range of temperature, i.e., improved Viscosity Index, while also showing lubricity, thermal and oxidative stability and pour point equal to or better than mineral oil. To match synthetic lubricants with their intended application, these lubricants have, in the past, been formulated for specific properties. For example, poly-alpha-olefins (PA) were produced from 1-decene polymerization over promoted $BF_3$ or $AlCl_3$ catalysts. PAOs which have usually very high VI and very low pour points and low traction coefficients are particularly desirable lubricants because they not only function effectively over a broad range of temperatures, but are also highly energy efficient. Synthetic fluids with high traction coefficients have, in the past, been considered to be a different group of synthetic fluids. Traction coefficients are usually dependent on the chemical compositions of the fluid, and the literature discloses a correlation between traction coefficient and pressure-viscosity coefficient, which is also related to oil film thickness. M. Muraki and Y. Kimura, *Traction Characteristics of Synthetic Hydrocarbon Oils,* 7 Journal of JSLE 119 (International Edition, 1986); Mobil EHL Guidebook, 3rd Edition, Commercial Marketing, Technical Publications, 3225 Gallows Road, Fairfax, Va. 22037. Generally, fluids with higher traction coefficient generate thicker films, which means better protection of machine parts and less wear and reduced metal fatigue. Fluids with high traction coefficients not only offer better lubricating protection, but also are useful as traction fluids, providing high power transmission at low slip.

Mechanisms such as automotive transmissions, automotive power steering pumps, shock absorbers, industrial hydraulic systems, and gear reducers contain power transmission fluids. These fluids must have relatively high resistance to shear, but must also be relatively noncorrosive toward the materials of construction used in the power transmission mechanism. Further, the fluids must resist degradation (e.g., oxidation) over extended periods of use. To meet these rigorous criteria, industry has turned to synthetic power transmission fluids, examples of which include Santotrac (a registered trademark of the Monsanto Corporation) and the Delvac 1 and Mobil 1 power transmission fluids (Delvac 1 and Mobil 1 are registered trademarks of Mobil Oil Corporation).

Viscosity Index (VI) is the most common measure that is applied to the decrease in viscosity of petroleum oils with increasing temperature. A series of Pennsylvania oils exhibiting relatively small change in viscosity with changing temperature is arbitrarily assigned a VI of 100, whereas a series of Gulf Cost oils whose viscosities change relatively greatly is assigned a VI of 0. From the viscosity measurements at 40° and 100° C., the VI of any oil sample can be obtained from detailed tables published by the ASTM (ASTM D-2270) 14 *Kirk-Othmer Encyclopedia of Chemical Technology* 489 (Wiley, 1981). U.S. Pat. No. 4,913,794 to Le et al. teaches a method for improving the Viscosity Index of a lubricant stock and is incorporated herein by reference for its discussions of Viscosity Index and lubricant upgrading processes.

U.S. Pat. No. 3,671,598 to Moore relates to the isomerization of adamantane-containing compounds in the presence of sulfuric acid to provide useful traction fluids.

U.S. Pat. No. 3,648,531 to Duling et al. teaches a traction drive containing a fluid comprising an alkyladamantane dimer or an alkyladamantanol dimer.

U.S. Pat. No. 3,671,600 to Moore teaches ethylation of an adamantane nucleus in the presence of a strong acid and $BF_3$ etherate.

U.S. Pat. No. 3,793,203 to Driscoll et al. discloses polyolefins, paraffins, and polar compounds containing a gem-dialkyl substituted back-bone structure which are useful as traction fluids.

U.S. Pat. No. 3,903,001 to Gates et al. and 4,180,466 to Newingham et al. teach synthetic lubricants for limited slip differentials.

U.S. Pat. No. 3,966,624 to Driscoll et al. relates to a hydrogenated polymeric traction fluid containing a light olefin oligomer and at least one saturated adamantane compound.

Oxygenated compounds from polyisobutylene (e.g., ketones, esters, and alcohols) useful as traction fluid components are taught in U.S. Pat. No. 3,972,941 to Driscoll et al. Example 6 at column 7 notes that the additives of the '914 patent can be blended with paraffinic or naphthenic lubricants or with synthetic naphthenes or adamantanes.

U.S. Pat. No. 3,972,243 to Driscoll et al. relates to polyolefins, paraffins, and polar compounds containing a gem-structured backbone structure which are useful as lubricant additives and traction fluid components.

The completely hydrogenated dimers of alpha-methylstyrene as disclosed in U.S. Pat. No. 3,994,816 to Wygant illustrate the well-known problem of low Viscosity Index in power transmission fluids. The temperature/viscosity data shown at column 6 for 2,4-dicyclohexyl-2-methylpentane containing 3% cyclic dimer indicate a Viscosity Index of about 9.

Traction fluids containing compounds having two adamantane nuclei linked through an alkylene radical are disclosed in U.S. Pat. No. 4,008,251 to Moore et al.

Fluorinated adamantanes have also been found to be useful traction fluids, as shown in U.S. Pat. No. 4,041,086 to Moore et al. Ethers of adamantane have similarly been found to be useful as traction fluids, as shown in U.S. Pat. No. 4,043,927 to Duling et al.

U.S. Pat. No. 4,329,529 to Nambu teaches a traction fluid produced by hydrogenating the alkylation product of styrene with xylene and/or toluene, and optionally with ethylbenzene.

U.S. Pat. No. 4,371,726 to Horita et al. relates to a traction fluid containing three substituted cycloalkane rings, while U.S. Pat. No. 4,675,459 to Yuasa et al. teaches a traction drive fluid comprising a base stock which contains compounds having fused cyclohexane and norbornene rings.

Similarly, U.S. Pat. No. 4,751,335 to Kubo et al. teaches a method for making a traction fluid by decomposing a compound having four aromatic rings.

Traction fluids comprising cis- and trans-perhydroacenaphthene are taught in U.S. Pat. Nos. 4,761,510 and 4,783,565 to Naruse et al.

Ester compounds containing one or two cyclic or bicyclic alkanes which are useful as traction fluids are disclosed in U.S. Pat. No. 4,786,427 to Dare-Edwards.

U.S. Pat. No. 4,889,649 to Murai et al. teaches a oxidatively stable traction fluid containing 2,4-dicyclohexyl-2-methylpentane, polycyclohexlalkane, and a perhydroindane derivative.

U.S. Pat. No. 5,043,503 to Del Rossi et al. discloses alkylated polycycloparaffinic compounds useful as lubricating stocks which are prepared by alkylating a polycycloparaffinic compound in the presence of a catalyst having a Constraint Index of from about 1 to about 10.

U.S. Pat. No. 5,053,568 to Chen teaches a lubricant additive and composition comprising the copolymer of 1-vinyladamantane and a 1-alkene having from about 4 to about 16 carbon atoms, wherein the copolymer has a Viscosity Index of at least about 80 and a kinematic viscosity of at least about 6 cS at 212° F.

U.S. Pat. No. 5,085,792 to Narihiko et al. relates to a synthetic traction fluid comprising two substituted cyclohexane nuclei connected through an ester linkage.

U.S. Pat. No. 5,107,041 to Abe et al. relates to a synthetic traction fluid derived from a 1,1-dicyclohexyl cycloalkane.

Many of the fluids described in the above patents have high traction coefficients, but typically have very low VI. For example, the hydrogenated dimer of alpha-methyl-styrene (2,4-dicyclohexyl-2-methylpentane) has a VI of only 9. Known adamantane-based traction fluids (discussed in U.S. Pat. Nos. 3,966,624, 3,648,531, 4,043,927, 4,008,251, 3,994,816, and 4,889,649) have high traction coefficients but very low Viscosity Indices and tend to lose their viscosities quickly as the operating temperatures increase. When the fluid loses its viscosity, it also loses its lubricating film and thus its protection capability. For these reasons, it would be beneficial to provide a fluid having a high traction coefficient and also high VI and low pour point, which would lubricate effectively over a wide operating temperature range.

Meeting the competing requirements of stability, lubricity, traction coefficient, good low temperature properties, and noncorrosivity has, in the past, required mixing an additive package of specialty chemicals with the base stock. Thus it would be desirable to provide a base stock which itself has a high Viscosity Index and low pour point.

SUMMARY OF THE INVENTION

The present invention provides a diamondoid-based composition having an unusually high Viscosity Index which is useful as a lubricant or traction fluid. The composition is also a useful blending component in combination with synthetic or petroleum-based lubricating stocks. This combination of properties is surprising and unexpected because it is generally accepted that base stocks which exhibit sufficient resistance to shear to be useful as power transmission fluids generally have Viscosity Indices within the range of from about −50 to about +50. The power transmission fluid taught in the Wygant '816 patent, cited above, exemplifies the well-known problem of low Viscosity Index in power transmission fluids, with a Viscosity Index of about 9.

The present invention provides a composition comprising at least about 10 different diamondoid compounds selected from the group consisting of methyl-substituted and ethyl-substituted adamantane, diamantane, triamantane, and higher homologs, wherein each of said selected diamondoid compounds comprises no more than about 10 weight percent of said composition, from which composition at least a portion of $C_9$- components have been removed. This composition is characterized by unusually high Viscosity Index (typically exceeding about 100) and very low pour point.

In a preferred embodiment, the invention provides a composition comprising at least about 15 different diamondoid compounds selected from the group consisting of methyl-substituted and ethyl-substituted adamantane, diamantane, and triamantane, wherein each of said selected diamondoid compounds comprises no more than about 7 weight percent of said composition, from which composition at least a portion of $C_9$- components have been removed. The composition preferably comprises from about 30 to about 70 weight percent substituted and unsubstituted adamantanes, from about 20 to about 60 weight percent substituted and unsubstituted diamantanes, and from about 3 to about 20 substituted and unsubstituted triamantanes. The composition may optionally comprise less than about 10 weight percent of adamantanes, diamantanes, or triamantanes.

The Viscosity Index for the composition consistently exceeds about 100. In preferred embodiments, the Viscosity Index exceeds about 110, and in a particularly preferred embodiment the Viscosity Index exceeds about 115.

The diamondoid-based composition of the invention may be produced by mixing individual diamondoid components, by blending mixtures of diamondoids, or by fractionating and treating a naturally occurring diamondoid mixture. U.S. Pat. No. 5,120,899 to Chen and Wentzek teaches a particularly preferred method for recovering a diamondoid-containing mixture from a natural gas stream, and is incorporated by reference as if set forth at length herein.

The composition of the invention typically contains less than about 10 weight percent $C_9$- components, preferably less than about 5 weight percent $C_9$- components. The composition preferably contains less than about 5 weight percent aromatics, and more preferably less than about 1 weight percent aromatics. The composition preferably contains a minimum of color bodies (also referred to as colorants) and may be treated with a sorbent such as activated carbon or activated alumina to remove such compounds. In a particularly preferred embodiment, the composition is substantially free of $C_9$- components, particularly $C_9$- aromatics.

The composition of the invention may be used neat or may be blended with a synthetic or petroleum-based lubricant stock. Examples of useful synthetic lubricant blending stocks are taught in U.S. Pat. Nos. 4,943,383 to Avery et al., 4,952,303 to Bortz et al., 4,962,249 to Chen et al., 4,967,029 to Wu, 4,967,032 to Ho et al., 4,990,709 to Wu, 4,990,718 to Pelrine, 4,990,238 to Cruzman et al., 4,992,189 to Chen et al., 4,995,962 to Degnan, Jr., et al., 5,012,020 to Jackson et al., 5,015,795 to Pelrine, 5,068,046 to Blain et al., and 5,095,165 to Hsia Chen. These patents are incorporated herein for teaching synthetic lubricant blending components.

EXAMPLES

The following Examples show the unusual combination of traction coefficient and Viscosity Index which characterizes the compositions of the present invention. The traction coefficient, f, is defined as $$f = \frac{F}{W} = \frac{\text{Traction force}}{\text{Normal force}}$$

which is analogous to the commonly used friction coefficient.

The compositions of Examples 1–6 (determined by GC and GC-MS) are described below in the Table. The alkyl substituents are numbered in accordance with the following structural diagrams:

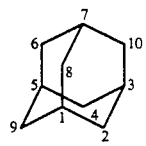
adamantane

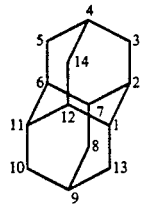
diamantane

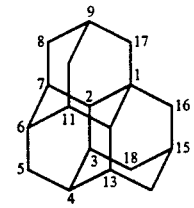
triamantane

The prefixes a-, e-, c-, and t- refer to the axial, equatorial, cis-, and trans- relationship of substituents in the same cyclohexane ring bearing the substituents in the diamondoids.

TABLE

| | Composition, Weight Percent | | | | | |
|---|---|---|---|---|---|---|
| Compounds | Example 1 | Example 2 | Example 3 | Example 4 | Example 5 | Example 6* |
| adamantane | 1.364 | None | None | None | None | 8.535 |
| 1-methyl adamantane | 5.615 | None | None | None | None | 22.362 |
| 1,3-dimethyl adamantane | 6.070 | None | None | None | None | 16.552 |
| 1,3,5-trimethyl adamantane | 2.438 | 0.001 | None | None | None | 4.413 |
| 1,3,5,7-tetramethyl adamantane | 0.413 | 0.001 | None | None | None | 0.428 |
| 2-methyl adamantane | 1.003 | None | None | None | None | 1.201 |
| t-1,4-dimethyl adamantane | 1.514 | 0.003 | None | None | None | 0.803 |
| c-1,4-dimethyl adamantane | 1.516 | 0.004 | None | None | None | 0.762 |
| 1,3,6-trimethyl adamantane | 1.774 | 0.019 | None | None | None | 0.507 |
| 1,2-dimethyl adamantane | 1.483 | 0.025 | None | None | None | 0.753 |
| 1r,3,4t-trimethyl adamantane | 2.056 | 0.094 | None | None | None | 0.528 |
| 1r,3,4c-trimethyl adamantane | 2.117 | 0.111 | None | None | None | 0.538 |
| 1,3,5,6-tetramethyl adamantane | 2.044 | 0.267 | None | None | None | 0.311 |
| 1-ethyl adamantane | 0.630 | 0.026 | None | None | None | 0.822 |
| 2,6-, 2e,4e-, 2e,4a-dimethyl adamantane | 0.118 | | None | None | None | 0.036 |
| 1,2,3,5-tetramethyl adamantane | 0.07 | | None | None | None | |
| 1-ethyl-3-methyl adamantane | 2.16 | 0.24 | None | None | None | 1.721 |
| 1,2,3-trimethyl adamantane | 0.34 | 0.05 | None | None | None | 0.064 |
| 1-ethyl-3,5-dimethyl adamantane | 1.582 | 0.350 | None | None | None | 0.881 |
| 1-ethyl-3,5,7-trimethyl adamantane | 0.424 | 0.064 | None | None | None | 0.314 |
| 1,2,3,5,7-pentamethyl adamantane | 1.050 | 0.413 | None | None | None | 0.386 |
| Other adamantanes* | 14.432 | 16.724 | None | None | None | 4.432 |
| Total adamantanes | 50.213 | 18.392 | 0.000 | 0.000 | 0.000 | 66.349 |
| diamantane | 3.967 | 5.774 | 0.274 | None | None | 7.485 |
| 4-methyl-diamantane | 5.345 | 12.057 | 0.374 | None | None | 6.277 |
| 4,9-dimethyl-diamantane | 1.710 | 3.851 | 0.170 | None | None | 1.210 |
| 1-methyl-diamantane | 3.343 | 7.576 | 0.796 | None | None | 3.275 |
| 2,4-dimethyl-diamantane | 2.078 | 4.726 | 0.481 | None | None | 1.115 |
| 1,4-dimethyl diamantane | 2.563 | 5.715 | 0.732 | None | None | 1.24 |
| 1,4,9-trimethyl diamantane | 1.103 | 2.623 | 0.376 | None | None | 0.58 |
| 3-methyl diamantane | 2.384 | 5.215 | 1.182 | None | None | 0.649 |
| 4,8-dimethyl diamantane | 1.618 | 3.577 | 0.838 | None | None | 0.251 |
| 3,4,9-trimethyl diamantane | 0.12 | 0.66 | 0.20 | None | None | 0.06 |
| 4-ethyl-diamantane | 0.584 | 1.187 | 0.922 | None | None | 0.124 |
| Other diamantanes | 16.477 | 27.586 | 53.938 | 3.405 | 4.591 | 3.482 |
| Total diamantanes | 41.292 | 80.547 | 60.283 | 3.405 | 4.591 | 25.748 |
| Triamantane | 1.175 | 0.330 | 7.777 | 5.673 | 7.713 | 0.496 |
| 9-methyl triamantane | 1.151 | 0.293 | 7.516 | 5.929 | 8.050 | 0.264 |
| 9,15-dimethyl triamantane | 0.233 | 0.051 | 1.420 | 1.375 | 1.554 | 0.039 |
| 3-Me & 3,9-diMe triamantanes | 0.696 | 0.120 | 4.067 | 5.789 | 7.335 | 0.086 |
| 7,9-diMe & 3,9,15-triMe triamantanes | 0.489 | 0.084 | 2.826 | 3.605 | 5.094 | 0.060 |
| 4-Me & 4,9,15-triMe triamantanes | 0.440 | 0.073 | 2.659 | 3.335 | 3.910 | 0.044 |
| 4,9- & 6,9-dimethyl triamantanes | 0.184 | 0.026 | 0.876 | 1.509 | 1.769 | 0.019 |

TABLE-continued

| Compounds | Composition, Weight Percent | | | | | |
|---|---|---|---|---|---|---|
| | Example 1 | Example 2 | Example 3 | Example 4 | Example 5 | Example 6* |
| 5-methyl triamantane | 0.289 | 0.044 | 1.599 | 3.082 | 3.948 | 0.015 |
| 5,9-methyl triamantane | 0.180 | | 0.824 | 1.760 | 1.949 | 0.009 |
| 8-Me & 5,9,15-triMe triamantanes | 0.244 | | 1.289 | 2.883 | 3.279 | |
| 9,14-dimethyl triamantanes | 0.114 | | 0.503 | 1.213 | 1.184 | |
| 8,9-dimethyl triamantanes | 0.069 | | 0.456 | 0.771 | 1.242 | |
| 16-methyl-, a diMe- & a triMe triamantanes | 0.366 | | 1.578 | 5.413 | 7.458 | |
| 2-methyl triamantane | 0.118 | | 0.401 | 2.820 | 2.093 | |
| other triamantanes | 1.857 | 0.040 | 5.882 | 41.321 | 33.799 | 0.050 |
| Total triamantanes | 7.605 | 1.061 | 39.673 | 86.478 | 90.377 | 1.082 |
| iso-tetramantane + A + B** | 0.119 | — | 0.044 | 3.075 | 1.334 | — |
| anti-tetramantane | 0.023 | — | — | 0.862 | 0.402 | — |
| other tetramantanes | 0.139 | — | — | 6.180 | 3.296 | — |
| Total tetramantanes | 0.281 | None | 0.044 | 10.117 | 5.032 | — |

*The sample evaluated in Example 6 contained 6.821 weight percent of materials having boiling points below that of adamantane.
**A and B are methyl- and dimethyl-iso-tetramantane, respectively.

EXAMPLE 1

Composition (wt. % from GC)

| | |
|---|---|
| Bridgehead methyl adamantanes | 15.9 |
| other adamantanes | 34.3 |
| diamantanes | 41.3 |
| triamantanes | 7.6 |
| tetramantanes | 0.3 |
| Viscosity: | 2.35 cS at 100° C. and 8.19 cS at 40° C. |
| VI: | 101 |
| Pour Point: | < −29° C. |

Traction (at 351510 psi maximum contact stress):

| Temperature °C. | 30 | 60 | 90 |
|---|---|---|---|
| Traction Coefficient: | 0.143 | 0.135 | 0.135 |

Volatility (by simulated distillation):

| Boiling points (°F.) | 535 | 550 | 570 | 620 | 650 | 735 |
|---|---|---|---|---|---|---|
| % | 1 | 5.5 | 20.5 | 60 | 78 | 100 |

EXAMPLE 2

Composition (wt. % from GC)

| | |
|---|---|
| adamantanes | 18.4 |
| diamantanes | 80.6 |
| triamantanes | 1.1 |
| Viscosity: | 3.21 cS at 100° C. and 12.24 cS at 40° C. |
| VI: | 117 |

EXAMPLE 3

Composition (wt. % from GC)

| | |
|---|---|
| diamantanes | 60.3 |
| triamantanes | 39.7 |
| Viscosity: | 4.92 cS at 100° C. and 24.69 cS at 40° C. |
| VI: | 126 |
| Pour Point: | −72° C. |

Traction (at 351510 psi maximum contact stress):

| Temperature °C. | 30 | 60 | 90 | 120 |
|---|---|---|---|---|
| Traction Coefficient: | 0.142 | 0.140 | 0.136 | 0.131 |

EXAMPLE 4

Composition (wt. % from GC)

| | |
|---|---|
| triamantanes | 90 |
| tetramantanes | 10 |
| Viscosity: | 9.11 cS at 100° C. and 70.98 cS at 40° C. |
| VI: | 103 |

Traction (at 351510 psi maximum contact stress):

| Temperature °C. | 30 | 60 | 90 | 120 |
|---|---|---|---|---|
| Traction Coefficient: | 0.141 | 0.142 | 0.136 | 0.133 |

EXAMPLE 5

Composition (wt. % from GC)

| | |
|---|---|
| diamantanes | 4.591 |
| triamantanes | 90.377 |
| tetramantanes | 5.032 |
| Viscosity: | 8.09 cS at 100° C. and 55.68 cS at 40° C. |
| VI: | 114 |
| Pour point: | −46° C. |

EXAMPLE 6

Composition (wt. % from GC)

| | |
|---|---|
| bridgehead methyladamantanes (0–4 Me) | 57.4 |
| other adamantanes | 14.0 |
| diamantanes | 27.4 |
| triamantanes | 1.2 |
| Viscosity: | 1.7 cS at 100° C. and 4.7 cS at 40° C. |
| VI: | 118 |

Traction (at 351510 psi maximum contact stress):

| Temperature °C. | 30 | 60 | 90 |
|---|---|---|---|
| Traction Coefficient: | 0.132 | 0.124 | 0.121 |

EXAMPLE 7

In comparison, the traction of Santotrac 50, a widely used commercial traction fluid, was evaluated under the same conditions as Example 6.

Traction (at 351510 psi maximum contact stress):

| Temperature °C. | 30 | 60 | 90 | 120 |
|---|---|---|---|---|
| Traction Coefficient: | 0.164 | 0.156 | 0.152 | 0.146 |

What is claimed is:

1. A composition containing less than about 5 weight percent C9- components, said composition comprising at least about 10 different diamondoid compounds selected from the group consisting of methyl-substituted and ethyl-substituted adamantane, diamantane, and triamantane, said composition comprising from about 30 to about 70 weight percent substituted and unsubstituted adamantanes, from about 20 to about 60 weight percent substituted and unsubstituted diamantanes, and from about 3 to about 20 weight percent substituted and unsubstituted triamantanes, wherein each of said selected diamondoid compounds comprises no more than about 10 weight percent of said composition.

2. The composition of claim 1 further comprising at least about 15 different diamondoid compounds selected from the group consisting of methyl-substituted and ethyl-substituted adamantane, diamantane, and triamantane, wherein each of said selected diamondoid compounds comprises no more than about 7 weight percent of said composition.

3. The composition of claim 1 containing less than about 10 weight percent substituted and unsubstituted adamantanes.

4. The composition of claim 1 containing less than about 10 weight percent substituted and unsubstituted diamantanes.

5. The composition of claim 1 containing less than about 10 weight percent substituted and unsubstituted triamantanes.

6. The composition of claim 1 further characterized by a Viscosity Index of at least about 100.

7. A composition comprising at least about 10 different diamondoid compounds selected from the group consisting of methyl-substituted and ethyl-substituted adamantane, diamantane, and triamantane, said composition comprising from about 30 to about 70 weight percent substituted and unsubstituted adamantanes, from about 20 to about 60 weight percent substituted and unsubstituted diamantanes, and from about 3 to about 20 weight percent substituted and unsubstituted triamantanes, wherein each of said selected diamondoid compounds comprises no more than about 10 weight percent of said composition from which composition at least a portion of $C_9$- components have been removed.

8. The composition of claim 7 further comprising at least about 15 different diamondoid compounds selected from the group consisting of methyl-substituted and ethyl-substituted adamantane, diamantane, and triamantane, wherein each of said selected diamondoid compounds comprises no more than about 7 weight percent of said composition.

9. The composition of claim 7 containing less than about 10 weight percent substituted and unsubstituted adamantanes.

10. The composition of claim 7 further comprising less than 1 weight percent of aromatics.

11. The composition of claim 7 which has been treated to remove colorants.

12. The composition of claim 7 which is substantially free of aromatics.

13. A lubricant comprising the composition of claim 1 and a synthetic lubricant stock or a petroleum lubricant stock.

14. A lubricant comprising the composition of claim 2 and a synthetic lubricant stock or a petroleum lubricant stock.

15. A lubricant comprising the composition of claim 7 and a synthetic lubricant stock or a petroleum lubricant stock.

16. A lubricant comprising the composition of claim 8 and a synthetic lubricant stock or a petroleum lubricant stock.

17. A method of operating a traction drive apparatus comprising applying a shear force to the composition of claim 1.

18. A method of operating a traction drive apparatus comprising applying a shear force to the composition of claim 7.

* * * * *